United States Patent [19]

Iwao et al.

[11] 4,264,620

[45] Apr. 28, 1981

[54] ANTIHYPERTENSIVE 5-SUBSTITUTED 2-PYRROLIDINECARBOXYLIC ACIDS

[75] Inventors: Jun-ichi Iwao, Takarazuka; Masayuki Oya, Osaka; Eishin Kato, Matsubara; Yoichi Kawashima; Hiroshi Masuda, both of Osaka; Tadashi Iso, Tondabayashi; Takihisa Chiba, Kyoto, all of Japan

[73] Assignee: Santen Pharmaceutical Co., Ltd., Osaka, Japan

[21] Appl. No.: 59,787

[22] Filed: Jul. 23, 1979

[30] Foreign Application Priority Data

Aug. 2, 1978 [JP] Japan .................. 53-94721

[51] Int. Cl.³ .................... A61K 31/40; C07D 207/16
[52] U.S. Cl. .......................... 424/274; 260/326.18 R; 260/326.34; 260/326.35; 260/326.36; 260/326.46; 260/326.43; 542/400; 546/281; 548/336
[58] Field of Search .................. 424/274; 260/326.43, 260/326.47, 326.46

[56] References Cited

U.S. PATENT DOCUMENTS

| 4,052,511 | 10/1977 | Cushman | 424/274 |
| 4,105,776 | 6/1978 | Ondetti et al. | 260/326.47 |
| 4,154,736 | 5/1979 | Ondetti | 260/326.12 R |

Primary Examiner—Mary C. Lee
Attorney, Agent, or Firm—Frishauf, Holtz, Goodman & Woodward

[57] ABSTRACT

Derivatives of 5-substituted 2-pyrrolidinecarboxylic acid which have the general formula

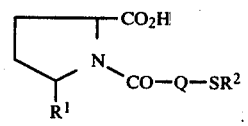

are useful in compositions as antihypertensive agents.

29 Claims, No Drawings

ANTIHYPERTENSIVE 5-SUBSTITUTED 2-PYRROLIDINECARBOXYLIC ACIDS

This invention relates to derivatives of 5-substituted 2-pyrrolidinecarboxylic acid and salts thereof which are useful as antihypertensive agents. These compounds are represented by the formula I

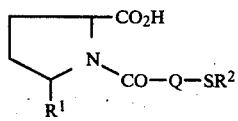

wherein $R^1$ is phenyl or hydroxyphenyl;

$R^1$ may be mercapto-lower alkyl, acylmercapto-lower alkyl, higher alkyl, higher alkenyl, cycloalkyl, aralkyl, aralkenyl, furyl, thienyl, imidazolyl, pyridyl, naphthyl, benzofuryl, benzothienyl, inodlyl, substituted higher alkyl, substituted higher alkenyl, substituted cycloalkyl, substituted aralkyl, substituted aralkenyl, substituted phenyl, substituted furyl, substituted thienyl, substituted imidazolyl, substituted pyridyl, substituted naphthyl, substituted benzofuryl, substituted benzothienyl, or substituted indolyl wherein the substituent(s) is lower alkyl, hydroxy-lower alkyl, hydroxy, mercapto, lower alkoxy, lower alkylenedioxy, acyloxy, acylmercapto, halogen, nitro, amino, lower alkylamino, acylamino or carboxy, except hydroxyphenyl;

$R^2$ is hydrogen or benzoyl;

Q is straight or branched alkylene with 1 to 3 carbon atoms (e.g. $-CH_2-$, $-CH(CH_3)-$, $-CH_2CH_2-$, $-CH(CH_3)CH_2-$);

in the formula I, lower alkyl, alkenyl or alkylene is saturated or unsaturated, straight or branched chain with 1 to 6 carbon atoms;

higher alkyl or alkenyl is saturated or unsaturated, straight or branched chain with 7 to 20 carbon atoms;

acyl is acetyl, pivaloyl, substituted or unsubstituted benzoyl, benzyloxycarbonyl, etc.;

aralkyl is benzyl, etc.;

The same shall be applied hereinafter.

The compounds of formula I of this invention are mercaptoacylamino acids and S-substituted mercaptoacylamino acids. Mercaptoacylamino acids have an inhibitory activity against angiotensin-converting enzyme and therefore they are useful as antihypertensive agents. S-Substituted mercaptoacylamino acids release mercaptoacylamino acids by enzymatic and/or chemical cleavage when administered to men or animals.

The compounds of formula I can be produced by the following methods.

An acid of the formula II

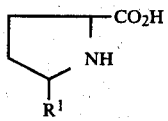

is reacted with a functional derivative of alkanoic acid of the formula III $$R^3S-Q-CO_2H \qquad (III)$$

by one of the known procedures wherein the compound III is activated by forming a mixed anhydride, symmetrical anhydride, acid chloride, active ester, etc. prior to reaction with the acid II to produce the compounds of the formula I. The resulting compound can then be converted to the compound of formula I, wherein $R^2$ is hydrogen, by hydrolysis or reduction (e.g. acid treatment with hydrochloric acid, p-toluenesulfonic acid, etc.; alkali treatment with sodium hydroxide, ammonia, etc.; catalytic reduction with palladium-carbon, etc.; alkaline metal treatment in liquid ammonia).

In another way, the compounds of formula I are produced by reacting an acid of formula II with a functional derivative of a haloalkanoic acid of the formula IV $$X-Q-CO_2H \qquad (IV)$$

and by reacting the resulting haloacid of the formula V

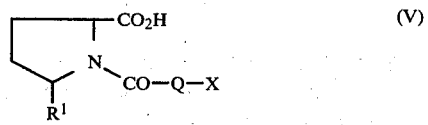

with thiobenzoic acid or benzylmercaptan. The resulting compound can then be converted to the compound of formula I, wherein $R^2$ is hydrogen, by hydrolysis or reduction in the same manner as above.

In the formulas (III, IV, and V), $R^3$ is benzoyl;

$R^3$ may be benzyl, alkyl- or phenylcarbamoyl;

X is halogen (e.g. bromine or chlorine).

The compounds of formula I synthesized by the above methods can form the conventional salts generally used as medicine such as sodium salt, potassium salt, calcium salt, aluminum salt, ammonium salt, diethylamine salt, triethanolamine salt, etc.

The compounds of formula I have the stereoisomers which are within the limit of this invention because they have asymmetric carbon atoms.

Examples are shown below, although this invention is not limited to these examples.

EXAMPLE 1

1-[(2S)-S-Benzoyl-3-mercapto-2-methylpropanoyl]-5-phenyl-2-pyrrolidinecarboxylic acid 22.8 g of 5-phenyl-2-pyrrolidinecarboxylic acid hydrochloride and 41.7 ml of triethylamine are dissolved in 700 ml of anhydrous acetone. To this solution, 24.3 g of (2S)-S-benzoyl-3-mercapto-2-methylpropanoyl chloride is added dropwise with stirring under ice-cooling. After the addition, the mixture is stirred under ice-cooling for 1 hour and at room temperature for another 1 hour. To the mixture, 5.7 ml of acetic acid is added, and the precipitate is removed by filtration. The filtrate is concentrated in vacuo and the produced oil is dissolved in 500 ml of ethyl acetate. The organic layer is washed with water and saturated sodium chloride solution, dried over magnesium sulfate, and concentrated in vacuo to give 53.8 g of oil. The oil is purified by silica gel column chromatography to give the titled compound, yield 30.2 g (76%), $[\alpha]_D^{29}$ −45.6° (c=1.0, methanol).

IR (CHCl$_3$, cm$^{-1}$) 1725, 1650, 1580, 910.

EXAMPLE 2

1-[(2S)-3-Mercapto-2-methylpropanoyl]-5-phenyl-2-pyrrolidinecarboxylic acid 20 g of 1-[(2S)-S-benzoyl-3-mercapto-2-methylpropanoyl]-5-phenyl-2-pyrrolidinecarboxylic acid is dissolved in 50 ml of methanol. To this solution 100 ml of conc. ammonia is added, and the mixture is stirred at room temperature for 1.5 hours. Excess ammonia and methanol are removed in vacuo, and the residue is washed with ethyl acetate. The aqueous layer is acidified with conc. hydrochloric acid, and extracted with ethyl acetate. The organic layer is washed with saturated sodium chloride solution, dried over magnesium sulfate, and concentrated in vacuo to give the titled compound, yield 8.5 g (58%), mp. 138.0°–142.5° C. (ethyl acetate), $[\alpha]_D^{29}$ −29.4° (c=1.0, methanol).

IR (nujol, cm$^{-1}$, to be applied hereinafter unless specified): 2650, 1740, 1600, 750, 705.

EXAMPLE 3

α- and β-1-(S-Benzoyl-3-mercaptopropanoyl)-5-(2-hydroxyphenyl)-2-pyrrolidinecarboxylic acid 12.2 g of 5-(2-hydroxyphenyl)-2-pyrrolidinecarboxylic acid hydrochloride and 9.6 g of sodium carbonate are dissolved in 200 ml of water. To this solution, 11.4 g of S-benzoyl-3-mercaptopropanoyl chloride is added dropwise with stirring under ice-cooling. After the addition, the mixture is stirred under ice-cooling for 1 hour and at room temperature for another 1 hour. This reaction solution is washed with ethyl acetate, acidified with conc. hydrochloric acid, and extracted with etyl acetate. The organic layer is washed with saturated sodium chloride solution, dried over magnesium sulfate, and concentrated in vacuo to give crystals (α-acid). The crystals are collected on a filter, yield 9.4 g (47%). The filtrate is concentrated in vacuo, and purified by silica gel column chromatography to give β-acid, yield 2.4 g (12%).

|  | α-acid | β-acid |
|---|---|---|
| mp. | 210–211° C. | — |
|  | (ethyl acetate-methanol) |  |
| IR | 3200, 1742, 1722, 1655, 1615, 1595, 1450, 1236, 1204, 912 | 1740, 1658, 1625, 1240, 1209, 915 (neat, cm$^{-1}$) |
| TLC: | Rf value$^{(a)}$ |  |
|  | 0.28 | 0.38 |

$^{(a)}$silica gel, benzene-ethyl acetate-acetic acid (25:25:1)

EXAMPLE 4

α- and β-5-(2-Hydroxyphenyl)-1-(3-mercaptopropanoyl)-2-pyrrolidinecarboxylic acid (i) 4.0 g of α-1-(S-benzoyl-3-mercaptopropanoyl)-5-(2-hydroxyphenyl)-2-pyrrolidinecarboxylic acid obtained in Example 3 is dissolved in 50 ml of methanol. To this solution, 50 ml of conc. ammonia is added, and the mixture is stirred at room temperature for 1.5 hours. Excess ammonia and methanol is removed in vacuo, and the residue is washed with ethyl acetate. The aqueous layer is acidified with conc. hydrochloric acid to give α-acid, yield 2.5 g (85%).

(ii) 2.0 g of β-1-(S-benzoyl-3-mercaptopropanoyl)-5-(2-hydroxyphenyl)-2-pyrrolidinecarboxylic acid obtained in Example 3 is dissolved in 20 ml of methanol. To this solution, 20 ml of conc. ammonia is added, and the mixture is treated in the same manner as (i) to give β-acid, yield 1.2 g (82%).

|  | α-acid | β-acid |
|---|---|---|
| mp. | 213–214° C. | 209–210° C. |
|  | (ethyl acetate-benzene) | (ethyl acetate-benzene) |
| IR | 3160, 1720, 1618, 1598, 1450 | 3180, 1718, 1620, 1600, 1450 |
| TLC: | Rf value$^{(b)}$ |  |
|  | 0.38 | 0.38 |

$^{(b)}$silica gel, ethyl acetate-ethanol-acetic acid (40:1:1)

EXAMPLE 5

α- and β-1-(S-Benzoyl-3-mercaptopropanoyl)-5-(4-hydroxyphenyl)-2-pyrrolidinecarboxylic acid The mixture of 12.2 g of 5-(4-hydroxyphenyl)-2-pyrrolidinecarboxylic acid hydrochloride, 9.6 g of sodium carbonate, 250 ml of water and 100 ml of ether, 11.4 g of S-benzoyl-3-mercaptopropanoyl chloride is added dropwise with stirring under ice-cooling. After the addition, the mixture is stirred under ice-cooling for 1 hour and at room temperature for another 1 hour. This reaction solution is acidified with conc. hydrochloric acid, and extracted with ethyl acetate. The organic layer is washed with saturated sodium chloride solution, dried over magnesium sulfate, and concentrated in vacuo to give crystals (α-acid). The crystals are collected on a filter, yield 6.2 g (31%). The filtrate is concentrated in vacuo, and purified by silica gel column chromatography to give β-acid, yield 3.6 g (18%).

|  | α-acid | β-acid |
|---|---|---|
| mp. | 164–166° C. | — |
|  | (ethyl acetate-methanol) |  |
| IR | 3170, 1714, 1654, 1611, 1206, 908 | 3340, 1750, 1653, 1207, 914 (neat, cm$^{-1}$) |
| TLC: | Rf value$^{(a)}$ |  |
|  | 0.22 | 0.32 |

$^{(a)}$Conditions are the same as Example 3.

EXAMPLE 6

α- and β-5-(4-Hydroxyphenyl)-1-(3-mercaptopropanoyl)-2-pyrrolidinecarboxylic acid (i) 4.0 g of α-1-(S-benzoyl-3-mercaptopropanoyl)-5-(4-hydroxyphenyl)-2-pyrrolidinecarboxyolic acid obtained in Example 5 is dissolved in 50 ml of methanol. To this solution, 50 ml of conc. ammonia is added, and the mixture is treated in the same manner as Example 2 to give α-acid, yield 2.2 g (74%).

(ii) 2.0 g of β-1-(S-benzoyl-3-mercaptopropanoyl)-5-(4-hydroxyphenyl)-2-pyrrolidinecarboxylic acid obtained in Example 5 is dissolved in 20 ml of methanol. To this solution, 20 ml of conc. ammonia is added, and the mixture is treated in the same manner as Example 2 to give β-acid, yield 0.8 g (54%).

| | α-acid | β-acid |
|---|---|---|
| mp. | 154–157° C. (ethyl acetate-benzene) | — |
| IR | 3300, 1746, 1594, 1239, 1188 | 3240, 1710, 1610, 1210 (neat, cm$^{-1}$) |
| TLC: | Rf value[a] 0.21 | 0.19 |

[a]Conditions are the same as Example 3.

EXAMPLE 7

α- and β-1-[(2S)-S-Benzoyl-3-mercapto-2-methylpropanoly]-5-(2-hydroxyphenyl)-2-pyrrolidinecarboxylic acid 12.2 g of 5-(2-hydroxyphenyl)-2-pyrrolidinecarboxylic acid hydrochloride and 9.6 g of sodium carbonate are dissolved in 200 ml of water. To this solution, 12.1 g of (2S)-S-benzoyl-3-mercapto-2-methylpropanoyl chloride is added dropwise with stirring under ice-cooling. After the addition, the mixture is stirred under ice-cooling for 1 hour and at room temperature for another 1 hour. This reaction solution is washed with ethyl acetate, acidified with conc. hydrochloric acid, and extracted with ethyl acetate. The organic layer is washed with saturated sodium chloride solution, dried over magnesium sulfate, and concentrated in vacuo to give crystals (α-acid). The crystals are collected on a filter, yield 9.2 g (44%). The filtrate is concentrated in vacuo, purified by silica gel column chromatography to give β-acid, yield 2.6 g (13%).

| | α-acid | β-acid |
|---|---|---|
| mp. | 204–205° C. (ethyl acetate-benzene) | — |
| $[α]_D^{25}$ | −16.5° (c = 1.0, methanol) | −41.6° (c = 1.0, methanol) |
| IR | 3310, 1713, 1668, 1621, 1598, 1446, 1209, 907 | 1739, 1655, 1620, 1600, 1450, 1208, 915 (neat, cm$^{-1}$) |
| TLC: | Rf value[b] 0.60 | 0.68 |

[b]Conditions are the same as Example 4.

EXAMPLE 8

α- and β-5-(2-Hydroxyphenyl)-1-[(2S)-3-mercapto-2-methylpropanoyl]-2-pyrrolidinecarboxylic acid (i) 4.1 g of α-1-[(2S)-S-benzoyl-3-mercapto-2-methylpropanoyl]-5-(2-hydroxyphenyl)-2-pyrrolidinecarboxylic acid obtained in Example 7 is dissolved in 50 ml of methanol. To this solution, 50 ml of conc. ammonia is added, and the mixture is treated in the same manner as Example 4 to give α-acid, yield 2.8 g (90%).

(ii) 2.1 g of β-1-[(2S)-S-benzoyl-3-mercapto-2-methylpropanoyl]-5-(2-hydroxyphenyl)-2-pyrrolidinecarboxylic acid obtained in Example 7 is dissolved in 25 ml of methanol. To this solution, 25 ml of conc. ammonia is added, and the mixture is treated in the same manner as Example 4 to give β-acid, yield 1.1 g (71%).

| | α-acid | β-acid |
|---|---|---|
| mp. | 241–242° C. (ethyl acetate-methanol) | 233–234° C. (ethly acetate-benzene) |
| $[α]_D^{25}$ | −22.0° | −56.8° |

| | α-acid | β-acid |
|---|---|---|
| IR | (c = 1.0, methanol) 3310, 1720, 1613, 1599, 1460 | (c = 1.0, methanol) 3320, 1723, 1616, 1600, 1462 |
| TLC: | Rf value[b] 0.54 | 0.55 |

[b]Conditions are the same as Example 4.

EXAMPLE 9

α$_1$-, β$_1$-, α$_2$-, and β$_2$-1-(S-Benzoyl-3-mercaptopropanoyl)-5-(2-hydroxyphenyl)-2-pyrrolidinecarboxylic acid 35.8 g of (±)-2-(2-hydroxyphenyl)-5-pyrrolinecarboxylic acid is reacted with 34.5 g of (−)-1,2-diphenylethylamine to give the diastereoisomer salt. The salt is fractionally recrystallized from ethanol to give (−)-2-(2-hydroxyphenyl)-5-pyrrolinecarboxylic acid (−)-1,2-diphenylethylamine salt, yield 20.0 g (57%), mp. 193°–194° C., $[α]_D^{26}$ −90.0° (c=1.0, methanol). The residual salt in the filtrate is fractionally recrystallized from chloroform to give (+)-2-(2-hydroxyphenyl)-5-pyrrolinecarboxylic acid (−)-1,2-diphenylethylamine salt, yield 18.0 g (51%), mp. 138°–140° C., $[α]_D^{26}$ −20.3° (c = 1.2, methanol).

Each salt is treated with sodium hydroxide to give sodium (−)-2-(2-hydroxyphenyl)-5-pyrrolinecarboxylate, yield 10.6 g, mp. 250° C. and over (dec.), $[α]_D^{27}$ −249.5° (c=0.6, water), and sodium (+)-2-(2-hydroxyphenyl)-5-pyrrolinecarboxylate, yield 7.9 g, mp. 250° C. and over (dec.), $[α]_D^{26}$ +249.4° (c=0.6, water).

(i) 6.82 g of sodium (−)-2-(2-hydroxyphenyl)-5-pyrrolinecarboxylate is dissolved in 120 ml of 0.5 N hydrochloric acid, and hydrogenated with 300 mg of platinum oxide to give (−)-5-(2-hydroxyphenyl)-2-pyrrolidinecarboxylic acid hydrochloride.

All of thus obtained product is dissolved in the mixture of 10.62 g of triethylamine, 300 ml of acetone and 15 ml of water. To the reaction mixture, 6.9 g of S-benzoyl-3-mercaptopropanoyl chloride is added dropwise with stirring under ice-cooling. After the addition, the mixture is stirred at room temperature for 1 hours, and acidified with hydrochloric acid. Acetone is removed, and then the mixture is extracted with ethyl acetate. The organic layer is washed with saturated sodium chloride solution, dried over magnesium sulfate, and evaporated to give oil. The oil is separated and purified by column chromatography to give α$_1$-acid, yield 5.91 g.

Another fraction is reacted with dicyclohexylamine to give β$_1$-acid dicyclohexylamine salt, yield 0.48 g.

| | α$_1$-acid | β$_1$-acid dicyclohexylamine salt |
|---|---|---|
| mp. | 89–92° C. (dec.) | 191–192° C. |
| $[α]_D^{25}$ | +47.4° (c = 1.0, methanol) | −11.2° (c = 0.5, methanol) |
| IR | 3400, 1750, 1660, 1575, 1200, 1175, 905 | 3300, 1655, 1630, 1555, 1400, 1195, 910 |
| TLC: | Rf value[a] 0.59 | 0.57 |

[a]silica gel, ethyl acetate-chloroform-acetic acid (7:5:1), to be applied hereinafter.

(ii) 6.82 g of sodium (+)-2-(2-hydroxyphenyl)-5-pyrrolinecarboxylate is treated in the same manner as i) to give α₂-acid, yield 4.7 g, and β₂-acid dicyclohexylamine salt, yield 0.15 g.

|  | $\alpha_2$-acid | $\beta_2$-acid dicyclohexylamine salt |
|---|---|---|
| mp. | 91–93° C. (dec.) | 192–193.5° C. |
| $[\alpha]_D^{25}$ | −49.8° (c = 0.9, methanol) | +11.6° (c = 0.5, methanol) |
| IR | 3400, 1750, 1660, 1575, 1200, 1175, 905 | 3300, 1655, 1630, 1555, 1400, 1195, 910 |
| TLC: | Rf value[a] 0.59 | 0.57 |

EXAMPLE 10

$\alpha_1$- and $\alpha_2$-5-(2-Hydroxyphenyl)-1-(3-mercaptopropanoyl)-2-pyrrolidinecarboxylic acid (i) 1.0 g of $\alpha_1$-1-(S-benzoyl-3-mercaptopropanoyl)-5-(2-hydroxyphenyl)-2-pyrrolidinecarboxylic acid is dissolved in 10 ml of conc. ammonia. The mixture is stirred at room temperature for 1 hour. Ammonia is removed, and then the mixture is washed with ethyl acetate. The aqueous layer is acidified with hydrochloric acid, and extracted with ethyl acetate. The organic layer is washed with saturated sodium chloride solution, dried over magnesium sulfate, and evaporated to give $\alpha_1$-acid, yield 0.58 g.

(ii) 1.0 g of $\alpha_2$-1-(S-benzoyl-3-mercaptopropanoyl)-5-(2-hydroxyphenyl)-2-pyrrolidinecarboxylic acid is treated in the same manner as (i) to give $\alpha_2$-acid, yield 0.58 g.

|  | $\alpha_1$-acid | $\alpha_2$-acid |
|---|---|---|
| mp. | 197–198° C. (dec.) (ethyl acetate-cyclohexane) | 198–199° C. (dec.) (ethyl acetate-cyclohexane) |
| $[\alpha]_D^{25}$ | +34.7° (c = 0.5, methanol) | −35.3° (c = 0.5, methanol) |
| IR | 3360, 1720, 1685, 1605, 1585, 1280, 1165, 760 | 3360, 1720, 1685, 1605, 1585, 1280, 1165, 760 |
| TLC: | Rf value[a] 0.58 | 0.58 |

The potent antihypertensive effect of the compound (I) and related salts of this invention is clear in the comparison of the pharmacological activity between the known compound and the compounds of this invention as explained below. The inhibitor of angiotensin-converting enzyme which converts biologically inactive decapeptide, angiotensin I, to active octapeptide, angiotensin II, is found to be useful as antihypertensive medicine. In view of the above, we investigated the pharmacological activities of the compounds of the present invention from the aspect of inhibitory activity against the enzyme.

PHARMACOLOGICAL TEST 1

As the method of measurement of angiotensin-converting enzyme activity, bioassay for the contractile response of isolated smooth muscle or the pressor response of normal animals and biochemical assay for the enzyme isolated from lung or other organs of animals are known. The former is found more advantageous than the latter for the examination of the convertion of angiotensin I to angiotensin II in vivo.

In the present study, therefore, we adopted the bioassay for contractile response of isolated guinea-pig ileum to angiotensin I.

Measurement of inhibitory activity of angiotensin-converting enzyme

Isolated guinea-pig ileum was suspended in the organ bath containing 20 ml of Tyrode's solution of 30° C. gassed with 95% $O_2$+5% $CO_2$. The contraction induced by the addition of angiotensin I (0.1 μg/ml) at intervals of 10 minutes was recorded on a recticorder (Nihon Koden) for 90 seconds using FD pick up (ST-1T-H, Nihon Koden).

The test compounds were added to the bath 5 minutes before the addition of angiotensin I.

The inhibitory activity of angiotensin-converting enzyme was calculated by the following formula.

$$\frac{A - B}{A} \times 100$$

A: contractile intensity of angiotensin I before addition of the compound

B: contractile intensity of angiotensin I after addition of the compound

From the fact that kininase II, which destroys bradykinin having contractile action of isolated guinea-pig ileum, is thought to be identical with angiotensin-converting enzyme, augmentation of the contractile response to bradykinin by test compounds was examined by using bradykinin (0.005 μg/ml) in place of angiotensin I according to the above mentioned method.

The results are shown in a table. All of the test compounds inhibited the contractile response to angiotensin I, while they enhanced the response to bradykinin.

PHARMACOLOGICAL TEST 2

The activity of angiotensin-converting enzyme was measured by spectrophotometry according to the method of Biochem. Pharmacol., 20. 1637 (1971). That is, the absorbance of hippuric acid was measured, which is liberated by incubating hippuryl-L-histidyl-L-leucine (HHL) as substrate in the presence of angiotensin-converting enzyme extracted from rabbit lung.

Measurement of inhibitory activity of angiotensin-converting enzyme

The reaction mixture is as follows:
100 mM phosphate buffer (pH 8.3)
300 mM sodium chloride
5 mM HHL
$10^{-3}$–$10^{-3}$ M enzyme inhibitor
5 mU enzyme 0.25 ml of the above mixture was incubated at 37° C. for 30 minutes and the reaction was stopped by adding 0.25 ml of 1 N hydrochloric acid. To this solution, 1.5 ml of ethyl acetate was added in order to extract hippuric acid. 1.0 ml of ethyl acetate layer was collected and evaporated to dryness, and the residue obtained was dissolved in 1.0 ml of water. The absorbance of this solution was measured at 228 nm.

The inhibitory activity of angiotensin-converting enzyme was calculated by the following formula:

$$\text{Percent inhibition} = \frac{A - B}{A} \times 100$$

A: absorbance of reaction solution before addition of the compound

B: absorbance of reaction solution after addition of the compound

Concentration of compound producing 50% inhibition of angiotensin-converting enzyme ($IC_{50}$)

The solution containing compounds at the concentration of $1 \times 10^{-3}$ M to $1 \times 10^{-9}$ M was incubated and percent inhibition at each concentration was calculated according to the above formula, and then $IC_{50}$, concentration of compound producing 50% inhibition of the enzyme activity, was determined.

The results are shown in a table.

The compounds examined in these tests are shown below.

The compounds of this invention

Compound A: α-5-(2-hydroxyphenyl)-1-(3-mercaptopropanoyl)-2-pyrrolidinecarboxylic acid Compound B: α-5-(4-hydroxyphenyl)-1-(3-mercaptopropanoyl)-2-pyrrolidinecarboxylic acid Compound C: α-5-(2-hydroxyphenyl)-1-[(2S)-3-mercapto-2-methylpropanoyl]-2-pyrrolidinecarboxylic acid Compound D: β-5-(2-hydroxyphenyl)-1-[(2S)-3-mercapto-2-methylpropanoyl]-2-pyrrolidinecarboxylic acid Compound E: $α_1$-5-(2-hydroxyphenyl)-1-(3-mercaptopropanoyl)-2-pyrrolidinecarboxylic acid Known compound Compound Z: (4R)-3-[(2S)-3-mercapto-2-methylpropanoyl]-4-thiazolidinecarboxylic acid

| Compound | Angiotensis I $IC_{50}$* (M) | Bradykinin $AC_{50}$ (M) | Angiotensin-converting enzyme $IC_{50}$* (M) |
|---|---|---|---|
| A | $1.7 \times 10^{-7}$ | $1.8 \times 10^{-9}$ | $5.6 \times 10^{-7}$ |
| B | $4.8 \times 10^{-7}$ | $9.8 \times 10^{-9}$ | $4.4 \times 10^{-7}$ |
| C | $1.6 \times 10^{-7}$ | $2.0 \times 10^{-9}$ | $1.1 \times 10^{-6}$ |
| D | $1.5 \times 10^{-7}$ | $2.6 \times 10^{-9}$ | $1.2 \times 10^{-6}$ |
| E | $7.6 \times 10^{-8}$ | $9.5 \times 10^{-10}$ | $6.5 \times 10^{-8}$ |
| Z | $1.7 \times 10^{-7}$ | $2.6 \times 10^{-9}$ | $2.6 \times 10^{31\ 7}$ |

*Concentration of compound producing 50% inhibition of the contractive action of angiotensin I on the guinea-pig ileum
**Concentration of compound producing 50% augmentation of the contractive action of bradykinin on the guinea-pig ileum
***Concentration of compound producing 50% inhibition against angiotensin-converting enzyme

TOXICITY TEST

Acute toxicity of compound A is low, that is the $LD_{50}$ value is 1000–1250 mg/kg.

(Experimental animals)

The male ddy-std strain mice (4 weeks of age, weighing 19–21 g) were placed in a breeding room of constant temperature and humidity (23±1° C., 55±5%) and fed freely pellet diet (CE-2, Clea Japan Inc.) and water ad. libitum for a week. The mice showing the normal growth were selected for the experiment.

(Method of administration)

Test compounds are suspended in 0.5% tragacanth solution, and administered intraperitoneally in a dose of 0.5 ml of 20 g body weight.

It is found from the above pharmacological tests that the compounds I of this invention are useful as antihypertensive agents. The compounds can be given with the combination of diuretics as other antihypertensive agents can generally at present. The dosage forms are tablet, capsule, granule, powder, suppository, injection, etc. In the treatment of hypertension, these preparations can contain not only general excipients but also other antihypertensive agents such as reserpine, α-methyldopa, guanethidine, clonidine, hydralazine, etc. The dose is adjusted depending on symptoms, dosage form, etc. But, usual daily dosage is 1 to 5000 mg, preferably 10 to 1000 mg, in one or a few divided doses.

The following are examples of formulation.

(1) Oral drug

| a. tablet | | |
|---|---|---|
| compound A | | 30mg |
| lactose | | 150mg |
| crystalline cellulose | | 50mg |
| calcium carboxymethylcellulose | | 7mg |
| magnesium stearate | | 3mg |
| | Total | 240mg |
| compound A | | 150mg |
| lactose | | 60mg |
| crystalline cellulose | | 30mg |
| calcium carboxymethylcellulose | | 7mg |
| magnesium stearate | | 3mg |
| | Total | 250mg |
| compound E | | 50mg |
| lactose | | 120mg |
| crystalline cellulose | | 60mg |
| calcium carboxymethylcellulose | | 7mg |
| magnesium stearate | | 3mg |
| | Total | 240mg |
| compound E | | 100mg |
| lactose | | 95mg |
| crystalline cellulose | | 45mg |
| calcium carboxymethylcellulose | | 7mg |
| magnesium stearate | | 3mg |
| | Total | 250mg |

The tablets may be treated with the common film-coating and further with sugar-coating.

| B. granule | | |
|---|---|---|
| compound A | | 30mg |
| polyvinylpyrrolidone | | 25mg |
| lactose | | 385mg |
| hydroxypropylcellulose | | 50mg |
| talc | | 10mg |
| | Total | 500mg |
| compound E | | 150mg |
| polyvinylpyrrolidone | | 20mg |
| lactose | | 280mg |
| hydroxypropylcellulose | | 40mg |
| talc | | 10mg |
| | Total | 500mg |
| c. powder | | |
| compound A | | 30mg |
| lactose | | 500mg |
| starch | | 440mg |
| colloidal silica | | 30mg |
| | Total | 1000mg |
| compound A | | 300mg |
| lactose | | 230mg |
| starch | | 440mg |
| colloidal silica | | 30mg |
| | Total | 1000mg |
| compound E | | 250mg |
| lactose | | 240mg |
| starch | | 480mg |
| colloidal silica | | 30mg |
| | Total | 1000mg |
| d. capsule | | |
| compound A | | 30mg |
| lactose | | 102mg |
| crystalline cellulose | | 56mg |
| colloidal silica | | 2mg |
| | Total | 190mg |

| | | |
|---|---|---|
| compound E | | 100mg |
| lactose | | 60mg |
| crystalline cellulose | | 38mg |
| colloidal silica | | 2mg |
| | Total | 200mg |
| compound A | | 200mg |
| glycerol | | 179.98mg |
| butyl p-hydroxybenzoate | | 0.02mg |
| | Total | 380mg |
| compound E | | 30mg |
| glycerol | | 349.98mg |
| butyl p-hydroxybenxoate | | 0.02mg |
| | Total | 380mg |

(2) Injection 1 to 30 mg of compound A or E is contained in 1 ml of the aqueous solution (pH 6.5–7.0).

What we claim is:

1. A compound of the formula

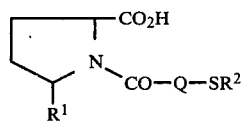

wherein $R^1$ is phenyl or hydroxyphenyl;

$R^2$ is hydrogen or benzoyl;

Q is straight or branched alkylene with 1 to 3 carbon atoms;

and pharmaceutically acceptable salts thereof.

2. A compound as in claim 1 wherein $R^1$ is phenyl, 2-hydroxyphenyl or 4-hydroxyphenyl.

3. A compound as in claim 2 wherein $R^2$ is hydrogen.

4. A composition comprising a compound of claim 1 in an amount sufficient to reduce blood pressure and at least one pharmaceutically acceptable excipient.

5. A method for reducing blood pressure which comprises administering an effective amount of a compound of claim 1.

6. A compound as in claim 2 wherein $R_2$ is benzoyl.

7. A compound as in any one of claims 1, 2, 3, and 6 wherein Q is —$CH_2CH_2$—.

8. A compound as in any one of claims 1, 2, 3 and 6 wherein Q is —$CH(CH_3)CH_2$—.

9. 1-[(2S)-S-Benzoyl-3-mercapto-2-methylpropanoyl]-5-phenyl-2-pyrrolidinecarboxylic acid of the formula of claim 1.

10. 1-[(2S)-3-Mercapto-2-methylpropanoyl]-5-phenyl-2-pyrrolidinecarboxylic acid of the formula of claim 1.

11. α-1-(S-Benzoyl-3-mercaptopropanoyl)-5-(2-hydroxyphenyl)-2-pyrrolidinecarboxylic acid of the formula of claim 1.

12. β-1-(S-Benzoyl-3-mercaptopropanoyl)-5-(2-hydroxyphenyl)-2-pyrrolidinecarboxylic acid of the formula of claim 1.

13. α-5-(2-Hydroxyphenyl)-1-(3-mercaptopropanoyl)-2-pyrrolidinecarboxylic acid of the formula of claim 1.

14. β-5-(2-Hydroxyphenyl)-1-(3-mercaptopropanoyl)-2-pyrrolidinecarboxylic acid of the formula of claim 1.

15. α-1-(S-Benzoyl-1-mercaptopropanoyl)-5-(4-hydroxyphenyl)-2-pyrrolidinecarboxylic acid of the formula of claim 1.

16. β-1-(S-Benzoyl-3-mercaptopropanoyl)-5-(4-hydroxyphenyl)-2-pyrrolidinecarboxylic acid of the formula of claim 1.

17. α-5-(4-Hydroxyphenyl)-1-(3-mercaptopropanoyl)-2-pyrrolidinecarboxylic acid of the formula of claim 1.

18. β-5-(4-Hydroxyphenyl)-1-(3-mercaptopropanoyl)-2-pyrrolidinecarboxylic acid of the formula of claim 1.

19. α-1-[(2S)-S-Benzoyl-3-mercapto-2-methylpropanoyl]-5-(2-hydroxyphenyl)-2-pyrrolidinecarboxylic acid of the formula of claim 1.

20. β-1-[(2S)-S-Benzoyl-3-mercapto-2-methylpropanoyl]-5-(2-hydroxyphenyl)-2-pyrrolidinecarboxylic acid of the formula of claim 1.

21. α-5-(2-Hydroxyphenyl)-1-[(2S)-3-mercapto-2-methylpropanoyl]-2-pyrrolidinecarboxylic acid of the formula of claim 1.

22. β-5-(2-Hydroxyphenyl)-1-[(2S)-3-mercapto-2-methylpropanoyl]-2-pyrrolidinecarboxylic acid of the formula of claim 1.

23. $α_1$-1-(S-Benzoyl-3-mercaptopropanoyl)-5-(2-hydroxyphenyl)-2-pyrrolidinecarboxylic acid of the formula of claim 1.

24. $β_1$-1-(S-Benzoyl-3-mercaptopropanoyl)-5-(2-hydroxyphenyl)-2-pyrrolidinecarboxylic acid of the formula of claim 1.

25. $α_2$-1-(S-Benzoyl-3-mercaptopropanoyl)-5-(2-hydroxyphenyl)-2-pyrrolidinecarboxylic acid of the formula of claim 1.

26. $β_2$-1-(S-Benzoyl-3-mercaptopropanoyl)-5-(2-hydroxyphenyl)-2-pyrrolidinecarboxylic acid of the formula of claim 1.

27. $α_1$-5-(2-Hydroxyphenyl)-1-(3-mercaptopropanoyl)-2-pyrrolidinecarboxylic acid of the formula of claim 1.

28. $α_2$-5-(2-Hydroxyphenyl)-1-(3-mercaptopropanoyl)-2-pyrrolidinecarboxylic acid of the formula of claim 1.

29. A compound as in any one of claims 1, 2, 3 and 6 wherein Q is —$CH_2$—.

* * * * *